United States Patent [19]

Kishimoto et al.

[11] Patent Number: 5,186,931

[45] Date of Patent: Feb. 16, 1993

[54] COMPOSITION AND METHOD FOR SUPPORTING BONE MARROW TRANSPLANTATION

[75] Inventors: Tadamitsu Kishimoto, No. 3-5-31, Nakano Tondabayashi-shi, Oosaka-fu; Toshio Hirano, Ibaraki; Yukio Akiyama, Kawasaki; Akira Okano, Kawasaki; Hiroshi Matsui, Kawasaki; Yoshiyuki Takahara, Kawasaki, all of Japan

[73] Assignees: Ajinomoto Co., Inc., Tokyo; Tadamitsu Kishimoto, Tondabayashi, both of Japan

[21] Appl. No.: 366,866

[22] Filed: Jun. 15, 1989

Related U.S. Application Data

[63] Continuation-in-part of Ser. No. 81,746, Aug. 5, 1987.

[30] Foreign Application Priority Data

| Aug. 6, 1986 | [JP] | Japan | 61-184858 |
| Aug. 27, 1986 | [JP] | Japan | 61-200433 |
| Dec. 18, 1986 | [JP] | Japan | 61-302699 |
| May 13, 1987 | [JP] | Japan | 62-116332 |
| Jun. 15, 1988 | [JP] | Japan | 63-147594 |
| Dec. 8, 1988 | [JP] | Japan | 63-310578 |

[51] Int. Cl.$^5$ .................. A61K 37/02; C07K 13/00
[52] U.S. Cl. .................. 424/85.2; 514/12; 530/350; 530/351
[58] Field of Search ............... 530/350, 351; 424/85.2, 424/85.1, 85.6; 514/12, 814.908

[56] References Cited

U.S. PATENT DOCUMENTS

| 4,730,036 | 3/1988 | Ralph et al. | 530/351 |
| 4,808,611 | 2/1989 | Cosman | 530/351 |
| 4,810,643 | 3/1989 | Souza | 530/351 |
| 4,965,195 | 10/1990 | Namen et al. | 435/91 |

FOREIGN PATENT DOCUMENTS

257406 3/1988 European Pat. Off. .

OTHER PUBLICATIONS

Watson et al, "Molecular Cloning of the Polypeptide Factors that Stimulate Growth, Maturation, and Function of Blood Cells", Molecular Biology of the Gene, vol. II, pp. 983–987 (4th ed. 1987).

Kolata, "Clinical Promise with New Hormones", Science, vol. 236, May 1, 1987, pp. 517–519.

Clark et al. "The Human Hematopoietic Colony-Stimulating Factors", Science, vol. 236, Jun. 5, 1987, pp. 1229–1237.

Hildeman, Essentials of Immunology, Elsevier, 1984, Title pg., Preface pg.

Oppenheim et al., Immunophysiology, Oxford U. Press 1990, Title pg., pp. IX, X, XI, 88, 98, 99, 101, 102.

Hirano, et al., Nature, vol. 324, Nov. 6, 1986, pp. 73 to 76.

G. G. Wong et al., The Journal of Immunology vol. 140, No. 9 (May 1, 1988) pp. 3040–3044 "Stimulation of murine hemopoietic colony formation . . . ".

T. Masaoka et al., Bone Marrow Transplantation, vol. 3 (Mar. 1988) pp. 121–127 "Administration of human urinary colony stimulating factor . . . ".

Ikebuchi et al, "Interleukin 6 enhancement of interleukin 3–dependent proliferation of multipotential hemopoietic progenitors." *Proc. Natl. Acad. Sci. USA*, vol. 84, pp. 9035–9039, Dec. 1987.

Koike et al, "Synergism of BSF-2/Interleukin 6 and Interleukin 3 on Development of Multipotential Hemopoietic Progenitors . . . ". *J. Exp. Med.*, vol. 168, pp. 879–890, Sep. 1988.

Laytor et al, "T Cell-Derived B Cell Growth (BCGF) and Differentiation (BCDF) Factors: Suppression of the Activity of BCDF . . . ". *J. Immunol.*, vol. 130(6), pp. 2502–2504, 1983.

Nakagawa et al, "Demonstration That Human B Cells Respond Differently to IL-2 and BCDF based on their stage of Maturation." *J. Immunol.*, vol. 137(10), pp. 3175–3182, Nov. 15, 1986.

*Primary Examiner*—Jeffrey E. Russel
*Attorney, Agent, or Firm*—Oblon, Spivak, McClelland, Maier & Neustadt

[57] ABSTRACT

A composition and a method for supporting bone marrow transplantation are disclosed. The composition comprises a therapeutically acceptable amount of human B cell differentiation factor, or its biological equivalent, optionally in combination with an auxiliary agent selected from IL-1, IL-3, IL-4, IL-5, G-CSF, GM-CSF, and M-CSF. The composition also promotes the proliferation of hematopoietic cells in vitro.

2 Claims, No Drawings

COMPOSITION AND METHOD FOR SUPPORTING BONE MARROW TRANSPLANTATION

The present application is a continuation-in-part of application Ser. No. 07/081,746, filed Aug. 5, 1987.

BACKGROUND OF THE INVENTION

1. Field of the Invention

The present invention relates to compositions for supporting bone marrow transplantation.

2. Description of the Background

Factors for differentiating mature B cells into antibody-producing cells in humans and mice are collectively called B cell differentiation factor (BCDF).

Human BCDF possesses activity which is important in the human body. Extensive research work in the recent past has led to the determination of the DNA sequence coding for BCDF and of the amino acid sequence of BCDF (Japanese Patent Application OPI Nos. 42688/88 and 56291/88). Further, human BCDF has been successfully produced using *E. coli* (Japanese Patent . Application OPI No. 157996/88).

It has been found that human BCDF can be used as an immunotherapeutic agent which is effective in the treatment of infectious diseases and cancers (Japanese Patent Application No. 289007/87). However, there has been no report in the literature of any pharmaceutical effects which human BCDF exhibits when it is administered in support of bone marrow transplantation (bone marrow transplantation is an effective treatment for diseases of hematopoietic organs such as leukemia, aplastic anemia, and the like).

Alternatives to the term human BCDF such as BSF-2 or interleukin 6 (IL-6) have been proposed (*Nature*, 324, 73 (1986), *EMBO. J.*, 6, 1219 (1987)). In the present text, however, the conventional term BCDF is used. Further, human BCDF as used herein does not possess interferon activity and is thus different from the IFN-$\beta_2$ standard which has interferon activity (European Patent Application Laid Open No. 0220574).

It is known that bone marrow contains multipotential hematopoietic stem cells (hereinafter identified as stem cells), although their quantity in bone marrow is small. These cells have the ability to differentiate into an all blood cell system, including lymphocytes. At the same time they also have self-renewal ability.

Blood cells have a limited life span. But the timely death of a blood cell is compensated for by the production of new blood cells. Stem cells in bone marrow maintain a constant number of blood cells in an organism through their self-renewal ability and continuing differentiation.

Therefore, where an abnormality in the quality of stem cells in an organism occurs for some reason, normal blood cell production is adversely affected. This causes irreversible desolation in the hematopoietic ability or immune capability of the organism.

The technique of bone marrow transplantation is used to transplant normal bone marrow cells, in which stem cells are present, into an organism to combat such a morbid state.

Deficient or diseased cells are replaced with cells derived from the normal. stem cells thereby curing the particular disease.

In 1951, Lorenz et al gave the theoretical basis for clinical application of bone marrow transplantation for the first time, reporting that the administration of bone marrow cells protected mice and guinea pigs exposed to lethal total-body irradiation (*J.N.C.I.*, 12, 197 (1951)).

In recent years, bone marrow transplantation has been used to treat various intractable hematopoietic diseases including leukemia and severe aplastic anemia. Many successful results have been reported. However, a limited number of patients participate in the benefits of this technique because the therapy is not safe and sure for all patients so treated (*TAISHYA*, 21, 899 (1984)). This is because numerous treated patients die due to serious complications caused by the transplantation itself, notwithstanding that various preventive measures are taken to protect the patient.

Major complications include graft versus host disease (hereafter simply referred to as GVHD), serious infections and interstitial pneumonia. For example, in the case of leukemia, death was observed in 202 out of 356 cases over the 10 year period of 1975 to 1985. A major cause of these deaths was the above stated complications, in spite of the fact that the patients received bone marrow transplantation (*TAISHYA*, 24, extra volume, *GANN* '87, 205 (1987)).

Why bone marrow transplantation is accompanied by the complications described above is as follows. In a patient suffering from leukemia, or the like, who receives bone marrow transplantation, the count of all leucocytes including malignant and normal leucocytes is reduced to zero by irradiation prior to the bone marrow transplantation operation. Irradiation is then followed by transplantation of bone marrow cells. After malignant leucocytes are eradicated by this operation, normal bone marrow cells are transplanted. The transplanted bone marrow cells function by producing a sufficient number of normal leucocytes. However, various complications such as infectious diseases occur during this time period up to when the transplanted bone marrow cells begin to function satisfactorily, namely, at the stage when normal leucocyte counts are reduced.

Therefore, a fundamental problem is how hematological and immunological reconstruction can be accelerated after bone marrow transplantation. Various supporting therapies such as the use of sterile rooms with sterile food, intestinal sterilization, constituent blood transfusion, and the like are normally employed upon bone marrow transplantation. In fact, attention has been directed to a recent development which is the clinical application of biologically active substances which act on the immune capability or hematopoiesis.

Other methodologies include the application of granulocyte colony stimulating factor (G-CSF) and urine-derived colony stimulating factor (CSF-HU) (*Nippon Rinsho*, 45, 2769 (1987)). However, the actions of these factors are mainly based on the differentiation of cells into mature granulocytes or monocytes.

Compositions and method for supporting bone marrow transplantation which are capable of causing the replication of stem cells which can accelerate hematological and immunological reconstruction important for bone marrow transplantation are yet unknown. A need therefore continues to exist for such a method.

SUMMARY OF THE INVENTION

Accordingly, an object of the present invention is to provide a composition and a method for supporting bone marrow transplantation which have the capability of causing the replication of stem cells, whereby complications which develop as a result of bone marrow transplantation in the treatment of the likes of leukemia can be prevented.

This object, and other objects of the invention hereinafter will become readily apparent from the description of the invention given hereinbelow, have been discovered by the inventors to be attainable by using a composition which contains human B cell differentiation factor (BCDF), or its biological equivalent, as the principle active ingredient. Such a composition may thus be advantageously employed in support of bone marrow transplantation.

used in the present invention includes one of the two following peptides having amino acid sequence (I) or (II) which are described, for example, in Japanese Patent Applications OPI Nos. 42688/88, 56291/88 and 289007/87.

| Amino acid sequence (I): | | | | | | | | | | |
|---|---|---|---|---|---|---|---|---|---|---|
| Pro | Val | Pro | Pro | Gly | Glu | Asp | Ser | Lys | Asp | Val |
| Ala | Ala | Pro | His | Arg | Gln | Pro | Leu | Thr | Ser | Ser |
| Glu | Arg | Ile | Asp | Lys | Gln | Ile | Arg | Tyr | Ile | Leu |
| Asp | Gly | Ile | Ser | Ala | Leu | Arg | Lys | Glu | Thr | Cys |
| Asn | Lys | Ser | Asn | Met | Cys | Glu | Ser | Ser | Lys | Glu |
| Ala | Leu | Ala | Glu | Asn | Asn | Leu | Asn | Leu | Pro | Lys |
| Met | Ala | Glu | Lys | Asp | Gly | Cys | Phe | Gln | Ser | Gly |
| Phe | Asn | Glu | Glu | Thr | Cys | Leu | Val | Lys | Ile | Ile |
| Thr | Gly | Leu | Leu | Glu | Phe | Glu | Val | Tyr | Leu | Glu |
| Tyr | Leu | Gln | Asn | Arg | Phe | Glu | Ser | Ser | Glu | Glu |
| Gln | Ala | Arg | Ala | Val | Gln | Met | Ser | Thr | Lys | Val |
| Leu | Ile | Gln | Phe | Leu | Gln | Lys | Lys | Ala | Lys | Asn |
| Leu | Asp | Ala | Ile | Thr | Thr | Pro | Asp | Pro | Thr | Thr |
| Asn | Ala | Ser | Leu | Leu | Thr | Lys | Leu | Gln | Ala | Gln |
| Asn | Gln | Trp | Leu | Gln | Asp | Met | Thr | Thr | His | Leu |
| Ile | Leu | Arg | Ser | Phe | Lys | Glu | Phe | Leu | Gln | Ser |
| Ser | Leu | Arg | Ala | Leu | Arg | Gln | Met | | | | or,

| Amino acid sequence (II): | | | | | | | | | | |
|---|---|---|---|---|---|---|---|---|---|---|
| Ala | Pro | Val | Pro | Pro | Gly | Glu | Asp | Ser | Lys | Asp |
| Val | Ala | Ala | Pro | His | Arg | Gln | Pro | Leu | Thr | Ser |
| Ser | Glu | Arg | Ile | Asp | Lys | Gln | Ile | Arg | Tyr | Ile |
| Leu | Asp | Gly | Ile | Ser | Ala | Leu | Arg | Lys | Glu | Thr |
| Cys | Asn | Lys | Ser | Asn | Met | Cys | Glu | Ser | Ser | Lys |
| Glu | Ala | Leu | Ala | Glu | Asn | Asn | Leu | Asn | Leu | Pro |
| Lys | Met | Ala | Glu | Lys | Asp | Gly | Cys | Phe | Gln | Ser |
| Gly | Phe | Asn | Glu | Glu | Thr | Cys | Leu | Val | Lys | Ile |
| Ile | Thr | Gly | Leu | Leu | Glu | Phe | Glu | Val | Tyr | Leu |
| Glu | Tyr | Leu | Gln | Asn | Arg | Phe | Glu | Ser | Ser | Glu |
| Glu | Gln | Ala | Arg | Ala | Val | Gln | Met | Ser | Thr | Lys |
| Val | Leu | Ile | Gln | Phe | Leu | Gln | Lys | Lys | Ala | Lys |
| Asn | Leu | Asp | Ala | Ile | Thr | Thr | Pro | Asp | Pro | Thr |
| Thr | Asn | Ala | Ser | Leu | Leu | Thr | Lys | Leu | Gln | Ala |
| Gln | Asn | Gln | Trp | Leu | Gln | Asp | Met | Thr | Thr | His |
| Leu | Ile | Leu | Arg | Ser | Phe | Lys | Glu | Phe | Leu | Gln |
| Ser | Ser | Leu | Arg | Ala | Leu | Arg | Gln | Met | | |

Amino acid sequence (I) is human BCDF. Amino acid sequence (II) is a polypeptide having a structure obtained by adding one Ala unit to human BCDF at the N-end thereof (hereafter referred to as human Ala-BCDF).

However, the BCDF employed in the present invention does not necessarily have to have one of the amino acid sequences (I) or (II) described above. That is, those peptides which have a structure formed by adding one or a plurality of amino acids to natural human BCDF at the N-end and/or C-end thereof and those peptides which have a structure in which one or a plurality of amino acids in the human BCDF structure are replaced by other amino acids can be used as the BCDF used in the present invention, so long as they have human BCDF activity. These peptides and human Ala-BCDF are all referred to in this text collectively as the biological equivalents of human BCDF.

Preferably, human BCDF or human Ala-BCDF is used. The content of the BCDF in the composition of the present invention is from about 0.0001 to about 100 wt %, preferably about 0.1 to about 1.0 wt %. This is an amount sufficient to support bone marrow transplantation.

Further the bone marrow transplantation-supporting composition of the present invention which contains BCDF as the effective ingredient may contain a carrier-protein such as serum albumin, or the like and an excipient such as mannitol, or the like. The bone marrow

DETAILED DESCRIPTION OF THE PREFERRED EMBODIMENTS

BCDF and a method for its production are disclosed in U.S. patent application Ser. No. 07/081,746, filed Aug. 5, 1987, which is hereby incorporated by reference.

As a result of extensive investigations to solve the above-described problems, the present inventors have found that compositions comprising human BCDF as the effective ingredient may be used advantageously for supporting bone marrow transplantation:

(1) can cause the replication of stem cells;

(2) can accelerate hematological and immunological reconstruction upon bone marrow transplantation to reconstruct even a small count of transplanted cells; and (3) enhance the survival rate upon bone marrow transplantation.

Thus the present invention relates to a composition which supports bone marrow transplantation, which employs human BCDF as the effective ingredient.

The human BCDF or its biological equivalent (collectively identified in this text as BCDF) which may be transplantation-supporting composition of the present invention may also contain, as an auxiliary agent one or more cytokinins other than BCDF, for example, interleukin 3 (IL-3), interleukin 1 (IL-1), interleukin 4 (IL-4), interleukin 5 (IL-5), granulocyte colony stimulating factor (G-CSF), granulocytemacrophage colony stimulating factor (GM-CSF) and macrophage colony stimulating factor (M-CSF), in addition to BCDF.

When such an auxiliary agent is incorporated in the composition, the effects of the composition in supporting bone marrow transplantation can increase synergistically. This is, IL-1, IL-3, IL-4, IL-5, G-CSF, GM-CSF and M-CSF can potentiate the augmentation of hematopoietic functions.

The amount of these auxiliary agents which are present is not particularly limited but may range from about 0.0001 to about 200000 wt%, based on 100 parts by weight of the BCDF. It must be emphasized that the amount of these auxiliary agents employed is not necessarily limited to the range described above but may be varied depending upon such factors as the age of the patient, and the like.

An auxiliary agent such as human IL-3, or the like does not always have to be administered as a drug together with BCDF at the same time. That is, these auxiliary agents may be administered at an appropriate time prior to or after administration of the bone marrow transplantation-supporting composition containing BCDF as the effective ingredient.

Of course, the bone marrow transplantation-supporting composition of the present invention may be administered to a patent in combination with other chemotherapeutic agents such as anticancer agents, antiviral agents, antibiotics, and the like.

The bone marrow transplantation-supporting composition of the present invention may be administered by intravenous injection or by intramuscular or subcutaneous injection. That is, the composition may be administered in any mode desired. The composition may also be administered at the time of bone marrow transplantation or after the bone marrow transplantation.

For purposes of treatment of a patient, BCDF may be administered at a dosage of 0.001 $\mu$g kg$^{-1}$ to 1,000 $\mu$g kg$^{-1}$, preferably 0.1 $\mu$g kg$^{-1}$ to 500 $\mu$g kg$^{-1}$, and most preferably 0.5 $\mu$g kg$^{-1}$ to 250 $\mu$g kg$^{-1}$.

When BCDF is administered together with an auxiliary agent, IL-1, IL-3, IL-4, IL-5, G-CSF, GM-CSF or M-CSF, the BCDF may be administered at one of the dosages noted above. The auxiliary agent is administered at a dosage of 0.001 $\mu$g kg$^{-1}$ to 1,000 $\mu$g kg$^{-1}$, preferably 0.01 $\mu$g kg$^{-1}$ to 500 $\mu$g kg$^{-1}$, and most preferably 0.1 $\mu$g kg$^{-1}$ to 250 $\mu$g kg$^{-1}$.

In another embodiment of the invention is that bone marrow cells or peripheral blood cells withdrawn from the patient or a donor may also be pretreated with the composition prior to bone marrow transplantation. That is, the bone marrow transplantation-supporting composition of the present invention can culture and proliferate stem cells even in vitro so that it is also possible to get the cells cultured in vitro back into the patient.

In in vitro use of BCDF to promote the growth of bone marrow cells, the BCDF may be added in an amount of from 0.1 ng ml$^{-1}$ to 1,000 ng ml$^{-1}$, preferably 1 ng ml$^{-1}$ to 500 ng ml$^{-1}$, and most preferably 10 ng ml$^{-1}$ to 100 ng ml$^{-1}$.

In this embodiment, the cells may be collected from human bone marrow or peripheral blood in a conventional manner. For example as shown in, Blood, 69, 953 (1987), cells may be obtained by using the density gradient method and adherent cells may further be removed therefrom. The stem cells may further be purified by treatment with antibodies, or the like. The cells may also be treated with anticancer agents such as 4-HC, VP-16, or the like, prior to incubation.

The stem cells may be artificially transformed. That is, any cell composition is usable so long as it contains stem cells. A medium for the incubation may be the likes of RPMI 1640, and Iscove modified MEM. It is desired to supplement the cells with 10 to 20% fetal calf serum. However, horse serum or human serum, may be employed as alternatives. Of course, no supplement may be used at all. If necessary, hydrocortisone, 2-mercaptoethanol, antibiotics, and the like may be added to the cells.

An initial cell density may be appropriately determined depending upon the proportion of stem cells in the cells which are to be employed. Culture conditions preferably are 33 to 37° C in the presence of 5 to 7.5% $CO_2$ and 5 to 20% of $O_2$ which conditions are normally used for the ordinary incubation of cells, but are not limited thereto.

As can be appreciated from the description above, the incubation procedure employed may be a conventional cell culture technique, except for the presence of added composition which supports the bone marrow transplantation.

The number of days over which the composition is added prior to bone marrow transplantation is not limited, but preferably is 1 to 11 days, more preferably 6 to 8 days.

By performing the so-called passage operation in which the cells are further diluted with a fresh medium on the way and the composition which supports bone marrow transplantation is added to the medium again, it is possible to continue culturing for a number of consecutive days and further increase the count of stem cells. The interval for the passage may be any number of days but 6 to 8 days are generally desired.

As described above, the bone marrow transplantation supporting composition of the present invention which contains BCDF is an extremely useful drug that can cause the growth of human hematopoietic stem cells important for bone marrow transplantation even in vitro.

Methods for maintaining stem cells in vitro, include a method in which stem cells are cultured in the co-presence of stroma cells (J. Cell. Physiol., 91, 335 (1977)) and a method which involves the addition of IL-3 (J. Clin. Invest., 76, 1613 (1985)). However, no method for replicating and proliferating stem cells has been known prior to the present invention.

According to the present invention, not only the amount of bone marrow cells to be collected from the donor can be reduced, but also hematological reconstruction after transplantation can be accelerated thereby preventing death of a treated patient as a result of infection.

It is known that autologous bone marrow transplantation has encountered problems in that bone marrow cells collected in advance should be stored by freezing, the number of stem cells is insufficient, the cells are contaminated with malignant cells, and the like, although the autologous bone marrow transplantation is advantageous in that GVHD does not generate. By applying the present invention to autologous bone marrow transplantation, the above problems can be solved.

The human BCDF used in the present invention may be any of those produced and purified from human T cells, B cells, fibroblasts, and the like, by known methods (*Proc. Natl. Acad. Sci., USA*, 82, 5490 (1985)). Also employable is BCDF produced by culturing transformants obtained by transforming a gene coding for human BCDF into an appropriate host such as *E. coli*, yeast, monkey cells (COS cells), hamster, bacteria, or the like, using a suitable vector and further purifying the transformants.

A detailed discussion of these production methods is provided, e.g., in Japanese Patent Applications OPI Nos. 115024/86, 42688/88, 56291/88 and 157966/88.

The bone marrow transplantation-supporting composition of the present invention containing BCDF as the effective ingredient principally accelerates immunological and hematological reconstruction. It is thus effective for treatment and prophylaxis of complications such as infections, and the like which accompany bone marrow transplantation.

The composition of the present invention is also advantageous in that the number of transplanted cells which are collected from a healthy donor can be reduced. In addition, it is also possible to pretreat bone marrow cells withdrawn prior to bone marrow transplantation with the composition of the present invention. That is, stem cells in the bone marrow cells are allowed to replicate and then the replicated stem cells can be transplanted.

Having generally described this invention, a further understanding can be obtained by reference to certain specific examples which are provided herein for purposes of illustration only and are not intended to be limiting unless otherwise specified.

EXAMPLE 1

Medical Preparation of Human BCDF

A HPLC fraction of human BCDF or human Ala-BCDF is allowed to stand at $-20°$ C. overnight and acetonitrile in the upper phase is removed. The lower phase is subjected to gel filtration with Sephadex G-25 or dialysis to remove the remaining acetonitrile and TFA and is substituted with PBS solution. The solution is diluted and, if necessary, serum albumin (0.1%) or serum (2 to 10%) from human or optionally from other mammal is added to the dilution. Thereafter, the system is filtered under sterile conditions to give human BCDF preparation or human Ala-BCDF preparation.

EXAMPLE 2

Replication of hematopoietic cells, hematopoietic precursor cells and stem cells by addition of human BCDF in vitro DBA/2 mouse-derived non-adherent bone marrow cells are prepared in $2.5 \times 10^5$/well (1 ml/well) and, human BCDF (100 ng/ml) and/or mouse IL-3 (200 units/ml) are supplemented to a RPMI 1640 medium containing 10% fetal calf serum followed by incubation for 6 days. Six days thereafter, the cultured cells are recovered and the hematopoietic cells are counted. Further, the hematopoietic precursor cells per $1 \times 10^4$ viable cells thus obtained are counted by the method described in Hematopoietic Stem Cell Experiment, page 40, published by Chugai Medical Publishing Co., Ltd. (1986), in terms of the number of colonies formed by culturing the cells in 0.8% methyl cellulose for 7 days together with 10% pokeweed mitogen-stimulated spleen cells conditioned medium. The experiment is carried out in 3 Petri dishes, whereby mean values and standard error are determined. Furthermore, the number of stem cells per $2 \times 10^5$ of viable cells is measured by the method of Till et al. (Radiat. Res., 14, 213 (1961)), using the mouse spleen colony-forming number as an index.

The results are shown in Table 1. As shown in Table 1, the counts of hematopoietic cells, hematopoietic precursor cells and stem cells significantly increases in the bone marrow cells cultured in the presence of human BCDF or mouse IL-3, in comparison to a control. Further, when the cells are cultured in the presence of both human BCDF and mouse IL-3, the counts of hematopoietic cells, hematopoietic precursor cells and stem cells synergistically increase. Similar results are also obtained using mouse bone marrow cells on Day 1 after administration of cancer chemotherapeutic agent, 5-fluorouracil, in a dose of 150 mg/kg.

The incubation time is changed within 3 to 11 days. The results reveal that the numbers of stem cells, and the like reached the maxima on Day 6 to Day 8.

Furthermore, the concentrations of human BCDF and mouse IL-3 are changed within 1 to 1000 ng/ml and within 1 to 1000 units/ml, respectively. As a result, the best effect is obtained with human BCDF at a concentration of 100 ng/ml or more and with mouse IL-3 at 200 units/ml.

The foregoing results reveal that human BCDF can increase the numbers of stem cells and the like by being added alone or in combination with IL-3 to the cells, prior to bone marrow transplantation.

TABLE 1

| Bone Marrow Cells | Factor Added | Hematopoietic Cells (count, $\times 10^{-3}$) | Hematopoietic Cell Precursors (count/ $10^4$ cells) | Stem Cells (count/ $2 \times 10^5$ cells) |
| --- | --- | --- | --- | --- |
| normal mouse | (before culture) | | | |
| | — | 250 | 90 ± 0 | 60 ± 0 |
| | (after culture) | | | |
| | None | 10 | 2 ± 1 | 1 |
| | Human BCDF | 23 | 90 ± 20 | 30 ± 20 |
| | Mouse IL-3 | 367 | 140 ± 10 | 40 ± 10 |
| | Human BCDF + Mouse IL-3 | 520 | 350 ± 40 | 120 ± 60 |
| mouse administered with 5-fluorouracil | (before culture) | | | |
| | — | 250 | 1.3 ± 0.3 | 20 ± 5 |
| | (after culture) | | | |
| | None | 0.7 | 1 | 1 |
| | Human BCDF | 0.8 | 6.7 ± 0.7 | 80 ± 20 |
| | Mouse IL-3 | 9.8 | 11.7 ± 6.7 | 200 ± 40 |
| | Human BCDF + Mouse IL-3 | 29.4 | 155 ± 30 | 467 ± 84 |

EXAMPLE 3

Increase in survival rate by transplantation of bone marrow cells cultured with human BCDF thereto in vitro Nine DBA/2 mice (female, 12 week age) are exposed to total-body irradiation, 900 rad (50 R/min.) of X ray.

Bone marrow cells (initial cell count of $2 \times 10^5$) cultured in Example 2 in the presence of human BCDF and mouse IL-3 are washed and then suspended in 500 $\mu$l of PBS containing 1% mouse serum. The cell suspension is intravenously transplanted to the mice from the tail control group, $2\times10^5$ of non-adherent bone marrow cells from syngeneic mice prepared in a conventional manner are transplanted. The survival rate at day 30 is shown in Table 2. Transplantation of the bone marrow cells cultured using human BCDF and mouse IL-3 significantly increased the survival rate after transplantation, in comparison to that of the control group.

TABLE 2

| Transplanted Cell | Survival Rate at day 30 |
|---|---|
| Cell conventionally prepared | 22% |
| Addition of cultured cell (without factors) | 0% |
| Addition of cultured cell (human BCDF + mouse IL-3) | 89% |
| No transplantation | 0% |

EXAMPLE 4

Increase in the number of hematopoietic cells and stem cells by administration of human BCDF in vivo.

An osmotic pump manufactured by Alza Co., Ltd. is filled with human BCDF, 70 μg (10 μg /mouse/day, for 7 days). A pump is implanted subcutaneously in each of 5 mice per group for continuous administration. Seven days thereafter, peripheral blood is collected and the spleen is removed from each mouse.

First, the count of blood cells in peripheral blood and the count of hematopoietic cells in the spleen are measured by the following methods. That is, with respect to blood, the count of leucocytes as an index of hematopoietic function is measured with an automatic blood cell counter (Toa Medical Electronics Co., Ltd.). Spleen hematopoietic cells are prepared from the spleen in a conventional manner and counted with a hemocytemeter. The spleen is also weighed.

Next, the total number of the stem cells and hematopoietic precursor cells in the spleen obtained by the methods described above is determined by the spleen colony formation method and the methyl cellulose method, respectively.

As shown in Table 3, the count of peripheral leucocytes and the count of hematopoietic cells in the spleen increases by continuous administration of human BCDF using the osmotic pump. Further, in the human BCDF administration group, the total count of stem cells markedly increases in comparison to the group which is not administered human BCDF. Also in bone marrow, similar results are obtained.

EXAMPLE 5

Recovery of hematopoietic function in mice bone marrow transplantation and administered human BCDF in vivo.

Five DBA/2 mice (female, 12 week age) are exposed to total-body irradiation, 750 rad (50 R/min.) of X ray. The cells employed for transplantation are bone marrow cells from syngeneic mice prepared in a conventional manner. The cells are suspended in PBS containing 1% mouse serum in predetermined cell densities ($5\times10^4$, $2\times10^5$, $1\times10^6$) and 500 μl each of the cell suspensions is intravenously transplanted into the mice from the tail vein within 6 hours after total-body irradiation. For 9 days from the day of transplantation, human BCDF is suspended in PBS containing 1% mouse serum in given concentrations (each 0.1 μg/mouse, 1.0 μg/mouse, 10, μg/mouse) and 100 μl each of the suspensions, are subcutaneously injected. On day 2, Day 4 and Day 9 after the transplantation, peripheral blood is collected through the heart of each mouse. Further, the spleen and femur which are hematopoietic organs in the living body are ectomized.

The hematopoietic function refers to the procedure in which stem cells are differentiated into hematopoietic precursor cells and the precursor cells are further differentiated into hematopoietic cells and blood cells.

Firstly, the number of blood cells and the number of hematopoietic cells in the spleen and the femur are measured by the following methods. Differential counts of leucocytes are made by preparing a smear sample in a conventional manner, staining the sample by Wright-Giemsa and then counting the cells microscopically. From the spleen and the femur, spleen hematopoietic cells and bone marrow hematopoietic cells are prepared in a conventional manner and counted with a hemocytometer. The spleen is also weighed.

As a result, on Day 9, when the hematopoietic function returns to normal level the recovery of leucocyte count is significantly accelerated when human BCDF is administered in doses of 1.0 μg/mouse and 10 μg/mouse, in comparison to the control group. The blood results on Day 9 in the representative 10 μg/mouse administration group are shown in Table 4. In general the recovery in the hematopoietic cell count after bone marrow transplantation is also dependent on the number of transplanted cells but, as shown in Table 5, the degree of recovery in the counts of spleen hematopoietic cells and bone marrow hematopoietic cells is equivalent to that of transplantation of the cell numbers by a factor of 4 to 5 times, upon administration of human BCDF.

TABLE 3

| | Peripheral Blood Leucocyte Count ($\times 10^2/\mu l$) | Spleen Weight (mg) | Spleen Hematopoietic Cell ($\times 10^6$ spleen) | Spleen Hematopoietic Precursor Cell ($\times 10^3$ spleen) | Stem Cell (count/spleen) |
|---|---|---|---|---|---|
| Normal Mouse | 40 ± 6 | 66 ± 10 | 45 ± 8 | 23 ± 2 | 6.300 ± 2,200 |
| Treated Mouse | | | | | |
| BCDF 0 g/day | 49 ± 18 | 79 ± 9 | 51 ± 4 | 28 ± 2 | 5,300 ± 1,900 |
| BCDF 10 μg/day | 84 ± 26* | 219 ± 19* | 113 ± 24* | 184 ± 10* | 44,000 ± 8,400* |

*indicates a statistical significance ($p < 0.05$)

TABLE 4

| Number of Transplanted Cells | Human BCDF | Differentiation | | | |
|---|---|---|---|---|---|
| | | Leucocytes ($\times 10^2/\mu l$) | Granulocytes ($\times 10^2/\mu l$) | Lymphocytes ($\times 10^2/\mu l$) | Monocytes ($\times 10/\mu l$) |
| 0 | — | 2.9 ± 1.0 | 0.3 ± 0.1 | 2.4 ± 0.9 | 2.4 ± 0.4 |
| 5 × 10⁴ | — | 2.4 ± 1.8 | 0.4 ± 0.3 | 1.7 ± 1.6 | 2.1 ± 2.5 |
| | + | 3.1 ± 0.7 | 0.5 ± 0.7 | 2.2 ± 0.7 | 3.9 ± 0.6 |
| 2 × 10⁵ | — | 3.8 ± 2.1 | 0.5 ± 0.4 | 3.0 ± 1.3 | 3.3 ± 2.1 |
| | + | 8.8 ± 4.3* | 1.6 ± 0.6* | 6.3 ± 4.6 | 9.3 ± 6.4 |
| 1 × 10⁶ | — | 7.3 ± 2.4 | 2.6 ± 1.3 | 3.8 ± 1.2 | 9.7 ± 5.3 |
| | + | 10.1 ± 7.7 | 5.3 ± 4.8 | 3.9 ± 2.5 | 8.6 ± 9.0 |
| Not exposed to X ray | | 41.5 ± 3.4 | 7.9 ± 1.5 | 32.0 ± 3.2 | 16.6 ± 10.5 |

*indicates a statistical significance ($p < 0.05$)

TABLE 5

| Number of Transplanted Cells | Human BCDF | Weight of Spleen (mg) | Count of Hematopoietic Cells | |
|---|---|---|---|---|
| | | | Spleen ($\times 10^6$/spleen) | Bone Marrow ($\times 10^6$/femur) |
| 0 | — | 17 ± 2 | 6.3 ± 0.8 | 0.2 ± 0.1 |
| 5 × 10⁴ | — | 34 ± 10 | 10.1 ± 2.3 | 0.6 ± 0.1 |
| | + | 44 ± 13 | 18.2 ± 3.4 | 2.1 ± 0.7* |
| 2 × 10⁵ | — | 76 ± 22 | 34.2 ± 5.2 | 1.2 ± 0.2 |
| | + | 127 ± 25* | 64.6 ± 22.4* | 3.4 ± 0.5* |
| 1 × 10⁶ | — | 86 ± 31 | 48.7 ± 25.0 | 4.4 ± 1.3 |
| | + | 116 ± 34 | 63.3 ± 38.7 | 4.0 ± 1.4 |
| Not exposed to X ray | | 93 ± 2 | 103.5 ± 24.2 | 7.6 ± 3.4 |

*indicates a statistical significance ($p < 0.05$)

Next, the total count of the stem cells and hematopoietic precursor cells in the spleen cells and bone marrow cells obtained by the methods described above is determined by the spleen colony formation method and the methyl cellulose method.

The total count of the stem cells and hematopoietic precursor cells indicates a marked recovery in the group administered human BCDF in comparison to the group which has not been administered human BCDF. For example, the stem cell count in the femoral bone marrow on Day 9 after the transplantation of $2 \times 10^5$ marrow cells has recovered to 1100 (normal value, 1500) in the group administered human BCDF in comparison to less than 60 in the group not administered human BCDF. The hematopoietic precursor cell count exhibits recovery to 5000 (normal value, 19000) in the group administered human BCDF in comparison to 1400 in the group not administered human BCDF. Similar recovery is noted in the spleen. The stem cell count exhibits recovery to 5100 (normal value, 4200) in the group administered human BCDF in comparison to 680 in the group not administered human BCDF. The hematopoietic precursor cell count exhibits recovery to 61200 (normal value, 40000) in the group administered human BCDF in comparison to 25000 in the group not administered human BCDF.

The foregoing results reveal that by administering human BCDF after bone marrow transplantation, hematological reconstruction of the transplanted mice is accelerated.

EXAMPLE 6

Increase in survival rate of mice upon bone marrow-transplantation and upon administration of human BCDF Bone marrow cells are transplanted into 8 to 10 mice 8 weeks of age which had been exposed to total-body body radiation in a manner similar to Example 5. The survival rate at day 21 is shown in Table 6. By administering human BCDF in a daily dose of 10 $\mu$g for 9 days, the survival rate is increased. Particularly in the group with less number of transplanted cells, a remarkable effect is noted.

TABLE 6

| Number of Transplanted Cells | Human BCDF (10 $\mu$g/day) | Survival Rate at day 21 (%) |
|---|---|---|
| 0 | — | 0 |
| 5 × 10⁴ | — | 20 |
| | + | 75 |
| 2 × 10⁵ | — | 50 |
| | + | 75 |
| 1 × 10⁶ | — | 75 |
| | + | 100 |

Obviously, numerous modifications and variations of the present invention are possible in light of the above teachings. It is therefore to be understood that within the scope of the appended claims, the invention may be practiced otherwise than as specifically described herein.

What is new and desired to be secured by Letters Patent of the United States is:

1. A method for promoting the proliferation of hematopoietic cells in vitro comprising treating bone marrow cells with an agent consisting essentially of human B cell differentiating factor or its biological equivalent with IL-3.

2. A method of treating a patient suffering from a disease of the hematopoietic organs, comprising administering to said patient a therapeutically effective amount of an agent consisting essentially of human B cell differentiation factor or its biological equivalent in combination with Il-3 in support of the treatment of the patient by bone marrow transplantation.

* * * * *

UNITED STATES PATENT AND TRADEMARK OFFICE
CERTIFICATE OF CORRECTION

PATENT NO. : 5,186,931
DATED : February 16, 1993
INVENTOR(S) : Kishimoto et al

It is certified that error appears in the above-indentified patent and that said Letters Patent is hereby corrected as shown below:

Column 1, line 24, after "Patent", delete "."; line 65, after "normal", delete ".";

Column 5, line 2, after "auxiliary agent", insert --,--;

Column 5, line 59, 60 and 62 and Column 6, lines 48 and 49;

Column 7, line 55; Column 8, line 62; and Column 12, lin 56, in all occurrences, "in vitro" should be --_in vitro_--.

Column 9, line 1 after "tail", insert --vein within 6 hours after total-body irradiation. As a--;

Column 9, line 22, delete "in vivo" insert -- _in vivo_--;

UNITED STATES PATENT AND TRADEMARK OFFICE
CERTIFICATE OF CORRECTION

PATENT NO. : 5,186,931
DATED : February 16, 1993
INVENTOR(S) : Kishimoto et al

It is certified that error appears in the above-indentified patent and that said Letters Patent is hereby corrected as shown below:

Column 9, Table 3, line 3, after "Cell (x $10^3$" insert --/--;

same line, after "Cell (x $10^3$" insert --/--;

Column 10, line 5, delete "in vivo", insert --<u>in vivo</u>--

Column 10, line 18, after "10" delete ",";

Column 11, line 67, delete the second occurrence of "body".

Signed and Sealed this

Twenty-seventh Day of September, 1994

BRUCE LEHMAN

Attest:

Attesting Officer

Commissioner of Patents and Trademarks